United States Patent
Pinchuk

Patent Number: 5,360,397
Date of Patent: Nov. 1, 1994

[54] HEMODIAYLSIS CATHETER AND CATHETER ASSEMBLY

[75] Inventor: Leonard Pinchuk, Miami, Fla.

[73] Assignee: Corvita Corporation, Miami, Fla.

[21] Appl. No.: 87,173

[22] Filed: Jul. 2, 1993

[51] Int. Cl.$^5$ .................................. A61M 1/00
[52] U.S. Cl. ........................... 604/27; 604/43; 604/266
[58] Field of Search ............... 604/27, 43, 174, 180, 604/266, 280, 284

[56] References Cited

U.S. PATENT DOCUMENTS

| | | | |
|---|---|---|---|
| 3,929,126 | 12/1975 | Corsqut | 604/43 |
| 4,134,402 | 1/1979 | Mahurkar | 128/214 R |
| 4,323,071 | 4/1982 | Simpson et al. | 128/343 |
| 4,583,968 | 4/1986 | Mahurkar | 604/43 |
| 4,692,141 | 9/1987 | Mahurkar | 604/43 |
| 4,871,357 | 10/1989 | Hsu et al. | 604/266 |
| 4,895,561 | 1/1990 | Kar | 604/43 |
| 4,935,006 | 6/1990 | Hasson | 604/43 |
| 5,188,593 | 2/1993 | Martin | 604/43 |

Primary Examiner—Jerome L. Kruter
Attorney, Agent, or Firm—David P. Gordon

[57] ABSTRACT

A hemodialysis catheter having a concentric outer lumen for inflow and a concentric inner lumen for outflow is disclosed. The hemodialysis catheter is used in conjunction with an adapter and with flexible extenders as a catheter assembly. The adapter has channels into which the concentric lumens extend and sealingly divides the lumens into a non-concentric branched arrangement. The flexible extenders couple to the branched lumens or to the adapter and may be doubled over and fastened in grooves in the adapter to stop fluid flow through the catheter. The flexible extenders preferably terminate in coupling mechanisms such as luer slips or luer locks. The catheter is provided with a soft atraumatic tip which has radial holes and a distal hole coupled to the inner lumen of the catheter. The outer lumen which terminates proximally of the tip also has radial holes. The catheter is preferably provided with a porous biocompatible and biostable polyurethane mesh along a portion of its outer surface which is intended to be in contact with the skin of the patient. The mesh may be sputter coated or impregnated with a bactericide.

37 Claims, 4 Drawing Sheets

HEMODIAYLSIS CATHETER AND CATHETER ASSEMBLY

BACKGROUND OF THE INVENTION

1. Field of the Invention

The present invention relates to surgical instruments for withdrawing fluid from or introducing fluids into a cavity of the body. The present invention more particularly relates to double lumen hemodialysis catheters and assemblies incorporating the catheters.

2. State of the Art

Hemodialysis catheters are catheters used to access blood for performing hemodialysis. The distal end of the catheter is inserted into an artery or vein of a patient, and the proximal end of the catheter is connected to a hemodialysis mechanism which causes the blood to flow through a hemodialysis membrane which filters the blood. The blood is then forwarded back to the proximal end of the catheter and then through the catheter and back into the artery or vein. The hemodialysis catheter must therefore have at least two lumens; one for the removal of blood; and the other for the return of the blood into the body. Pumps coupled to the hemodialysis mechanism are typically utilized for causing the blood to flow through the circuitous path.

Many types of hemodialysis catheter assemblies are known in the art. Examples of such catheter assemblies are seen in U.S. Pat. Nos. 4,314,402, 4,692,141, and 4,895,561 to Mahurkar. A representation of a similar catheter assembly is seen in prior art FIGS. 1 and 1a hereof. In particular, the hemodialysis catheter assembly 10 of FIGS. 1 and 1a is comprised of a double "D" cannula 12 (see FIG. 1a) with proximal and distal ends, a Y connector 14 coupled to the proximal end of the cannula 12, two flexible extenders 16a, 16b which coupled to the Y connector 14 and terminate in male luer slips or locks 18a, 18b, and two pinch stopcocks 20a, 20b which are used to pinch off the flexible extenders 16a and 16b when blood flow is not desired. Typically, a wing attachment device 22 is provided toward the proximal end of the cannula 12. The wing attachment device 22 is provided with holes 23 so that the wing attachment device 22 and hence the catheter 12 may be sutured to the skin of the patient.

As may be seen by close examination of prior art FIGS. 1 and 1a, the cannula 12 is a double D extrusion having an outlet lumen 12a and an inlet lumen 12b. The outlet lumen 12a of cannula 12 typically has a distal opening 24a, and sometimes includes side holes 25a. Likewise, the inlet lumen 12b of cannula 12 has side openings or ports 25b. Typically, blood is pumped from a vein through holes 25b into lumen 12b of catheter 12, and then through the Y connector 14, extender 16b, luer 18b and into the dialyzer (not shown) where the blood is filtered. The filtered blood is returned through luer 18a, extender 16a, Y connector 14 into lumen 12a of catheter 12 and out through opening 24a and holes 25a.

While the hemodialysis catheter assemblies of the art are extremely useful for patients who must undergo regular treatments, they still suffer from various drawbacks. First, the pincers which are used as valve means are unsightly, cumbersome, and uncomfortable to the patient, and most particularly so when used in the jugular vein of the neck. Second, the double D configuration of the catheter allows blood to be sucked from only one side of the catheter. If the catheter happens to be flush against the wall of a blood vessel with the suction hole against the wall, then blood will not easily flow into the catheter. Third, with the catheter configuration of the prior art, when blood is expelled from the tip of the catheter, it must be through a narrow opening. If a side hole, such as shown in prior art FIG. 1a is used to increase the outflow, the outflow through the side hole further pushes the cannula against the wall of the vessel and prevents inflow. Fourth, the materials used in the prior art hemodialysis catheters have dictated that the hemodialysis catheters be replaced periodically because the materials in contact with the skin either disintegrate or because the tissue may degrade the material or the entry site though the skin may become infected. Also, the tips of the prior art hemodialysis catheters tend to be relatively hard and sharp and often tend to traumatize the blood vessels during insertion and manipulation. Fifth, the hemodialysis catheters of the prior art tend to clog with coagulations (clots) of blood between uses. In order to dissolve or remove the clots, heparin flushes are required. However, not only do the heparin flushes require the time of a skilled practitioner, but they are not always effective.

SUMMARY OF THE INVENTION

It is therefore an object of the invention to provide a hemodialysis catheter assembly which is comfortable to the patient.

It is another object of the invention to provide a hemodialysis catheter with inflow and outflow lumens which are not readily subjected to clogging or blockage.

It is a further object of the invention to provide a hemodialysis catheter assembly which may remain in a patient for long periods of time.

An additional object of the invention is to provide a hemodialysis catheter with an atraumatic tip.

Another object of the invention is to provide a hemodialysis catheter assembly which is not unsightly, and which is easy to use and relatively comfortable for the patient.

A further object of the invention is to provide a hemodialysis catheter where the lumens of the catheter are concentric and are not readily subject to clogging or blockage, and where the tip of the catheter is atraumatic.

Yet another object of the invention is to provide a hemodialysis catheter assembly where the bending of soft, resilient extension tubes which extend from the catheter serves as a valve mechanism, and a flat disk which receives the catheter also serves to hold the soft resilient extension tubes in the closed position.

Even a further object of the invention is to provide a hemodialysis catheter with a slow release mechanism for releasing anticoagulants into the catheter when the patient is not undergoing hemodialysis.

In accord with the objects of the invention, a hemodialysis catheter generally comprises a catheter having concentric lumens for inflow and outflow. Preferably, the outer lumen of the concentric lumens is for inflow with radial holes being supplied at the distal end of the outer lumen for receiving the blood, while the inner lumen is for outflow, with radial holes and a hole in the end of the tip. The outer lumen preferably terminates proximally of the distal end of the inner lumen with the distal end of the inner lumen being enveloped in a soft atraumatic tip through which the holes extend. The catheter is also preferably provided with a porous polyurethane mesh along a portion of its outer surface which is intended to be in contact with the skin (fascia) of the patient and to encourage ingrowth. The porous polyurethane may contain if desired a bactericide or antibiotic to minimize infection. The polyurethane mesh is both biocompatible and substantially biostable so that the catheter may remain in the patient without disintegrating and without causing infection. According to a preferred aspect of the hemodialysis catheter, the outer lumen has a larger area then the inner lumen as it has been determined that fluid flow is expedited thereby.

The catheter assembly utilizes the hemodialysis catheter summarized above and further includes an adapter means and flexible extenders. The adapter means has channels into which the concentric lumens extend and sealingly divides the lumens into a non-concentric branched arrangement. The flexible extenders couple to the branched lumens or to the adapter means. The flexible extenders are sufficiently flexible such that they may be kinked (i.e., doubled over) to stop fluid flow, and the adapter means of the catheter is preferably provided with channels or grooves which receive the flexible extenders and hold them in the kinked position. The flexible extenders preferably terminate in coupling mechanisms such as luer slips or luer locks.

Other preferred aspects of the invention include: providing the catheter with a winged fixation device with holes for suturing; implementing the adapter means as a small flat disk with inner channels for the catheter lumens and outer grooves for the flexible extenders; sputter coating or impregnating the polyurethane mesh with a bactericide; and providing the outer lumen with a slow release anticoagulant reservoir.

Additional objects and advantages of the invention will become apparent to those skilled in the art upon reference to the detailed description taken in conjunction with the provided figures.

BRIEF DESCRIPTION OF THE DRAWINGS

FIG. 1a is a view at 1a-1a through the hemodialysis catheter of FIG. 1;

DETAILED DESCRIPTION OF THE PREFERRED EMBODIMENT

Figure 1:
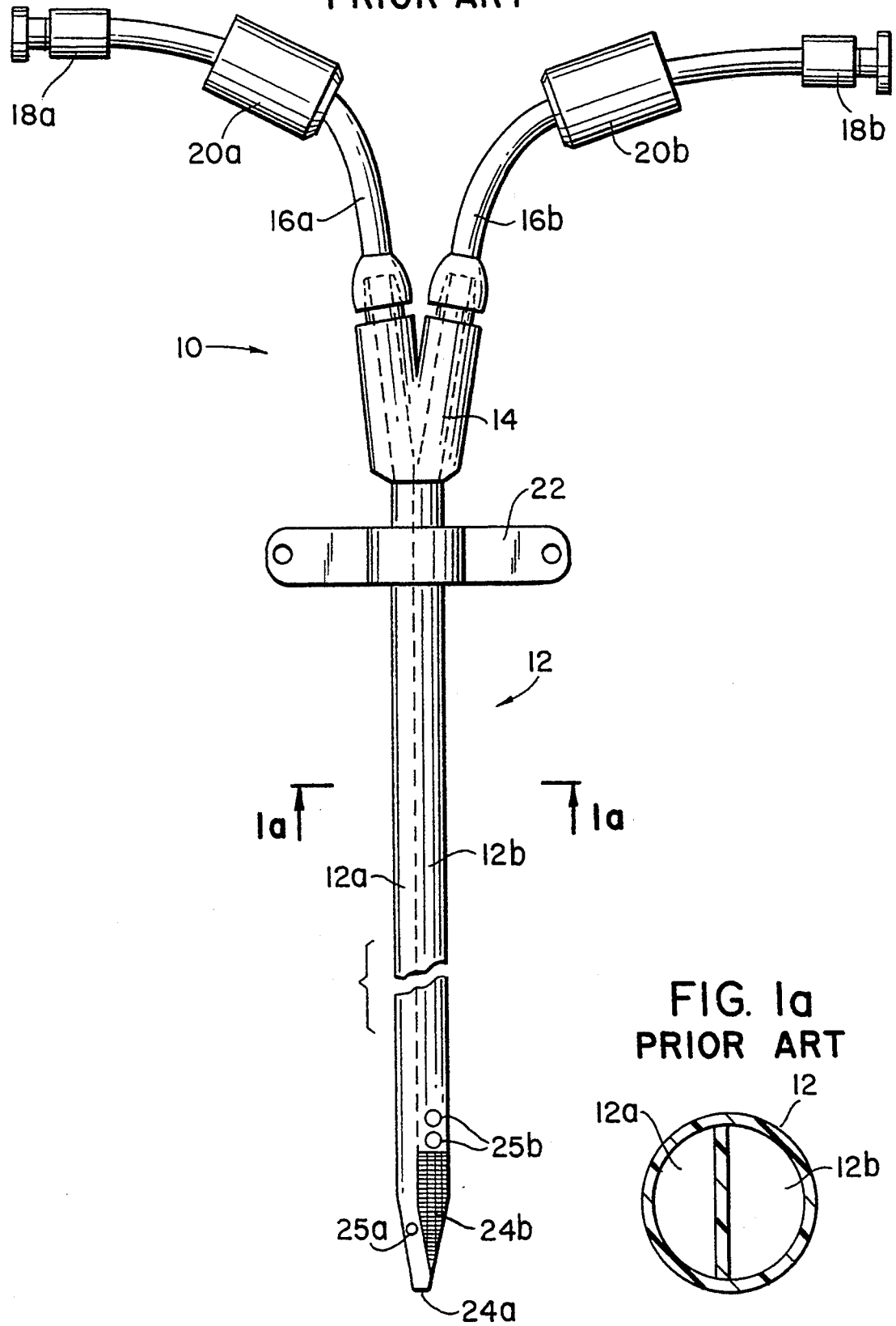
FIG. 1 is an enlarged schematic diagram of a typical prior art hemodialysis catheter assembly.

Turning to FIGS. 2, 2a-2c, and 3, the preferred hemodialysis catheter assembly 40 of the invention is seen. The catheter assembly 40 includes catheter 50, catheter adapter 52, and flexible extenders 53a, 53b. The catheter 50 is generally comprised of concentric lumens 50a and 50b, and preferably further includes a strain relief 54, a mesh sleeve 56, and a winged fixation device 58.

Figure 2:
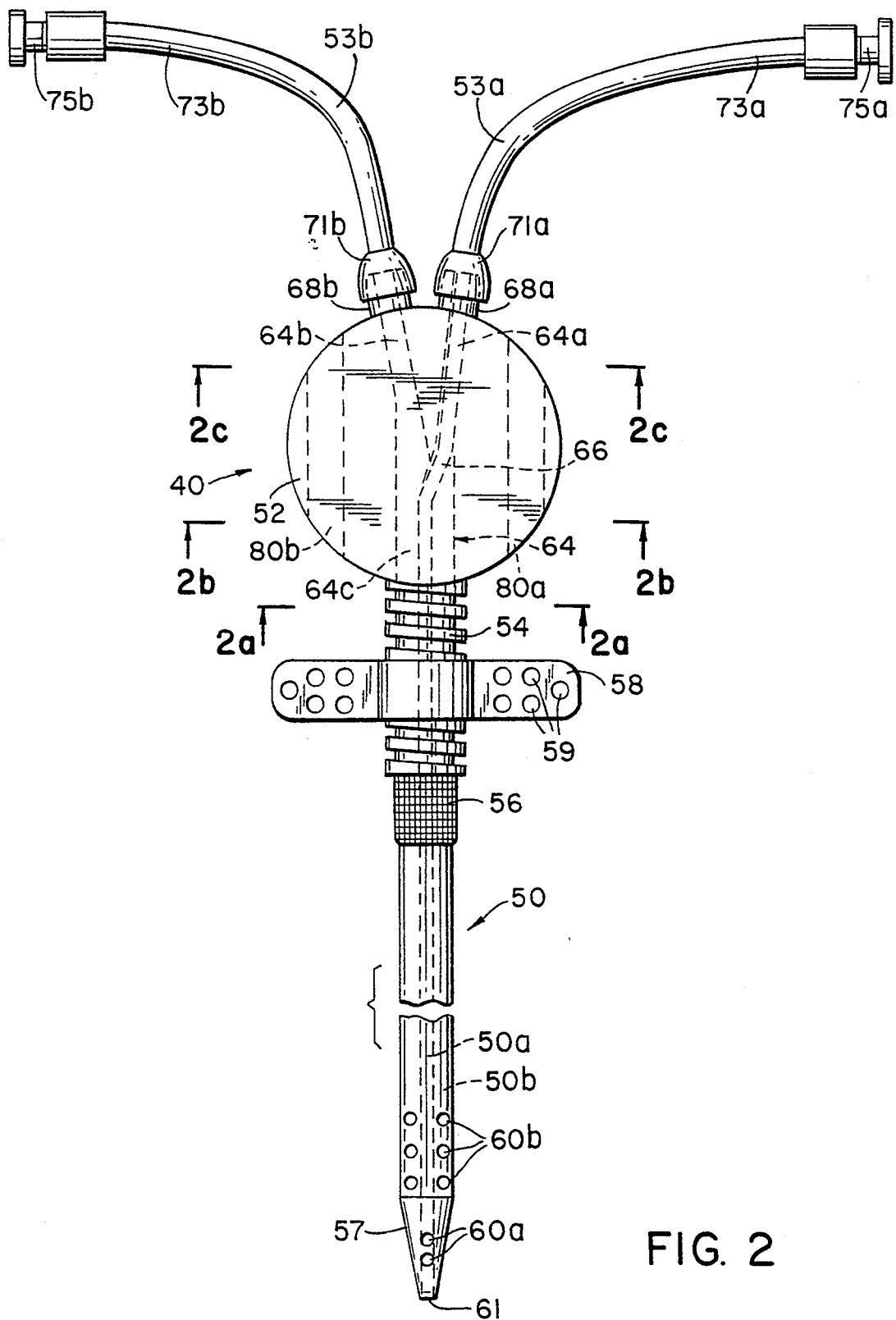
FIG. 2 is an enlarged schematic diagram of the hemodialysis catheter and catheter assembly of the invention in a flow-through position.
Figure 2A:
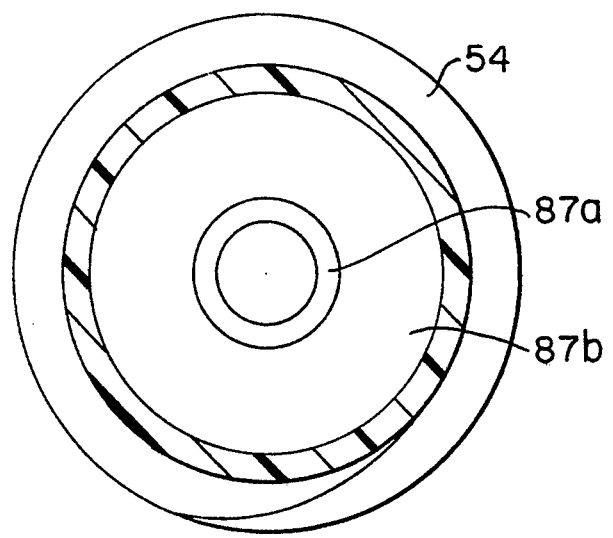
FIGS. 2a, 2b and 2c are views through indicated locations of the hemodialysis catheter and catheter assembly of FIG. 2.

The lumens 50a and 50b of catheter 50 are preferably made from a thin biocompatible and biostable material such as, e.g., polyurethane, or polycarbonate urethane. A Shore 80A to 55D Durometer polyurethane is preferred. The lumens 50a and 50b are generally concentric, with inner lumen 50a being preferably utilized for outflow and outer lumen 50b being utilized for inflow. As seen in FIG. 2, the inner lumen 50a extends beyond the outer lumen 50b with the inner lumen 50a terminating inside a solid tip 57, and the outer lumen 50b terminating at the proximal end of the solid tip 57. The solid tip 57 is preferably made from polyurethane, and may include a radiopaque formulation or filler such that the tip of the cannula can be observed under fluoroscopy. As described hereinafter, the proximal end of the tip 57 may also contain an anticoagulant drug reservoir.

The distal end of the outer lumen 50b of the preferred embodiment has radial holes 60b therethrough for receiving blood. Preferably, two or three sets of four holes extending around the lumen are provided, with the total area of the holes being at least equal to the cross sectional area of annular lumen 50b. The provision of radial holes around the outer lumen 50b permits blood to be pumped in from all sides, thus preventing the sucking in of the blood vessel wall. The inner lumen 50a is likewise provided with one or more sets of radial holes 60a which extend radially through the tip section 59. With the radial holes, when blood is flowing out of the holes, the catheter 50 is forced toward the center of the blood vessel in which it is located. A distal hole 61 at the distal end of the tip 59 is also provided for the exit of the blood. It will be appreciated that the tip section of the catheter is preferably provided with holes which match holes 60a, and the tip can be insert molded, heat fused, or injection molded, and then heat fused or solvent bonded in place over the inner lumen 50a and to the distal end of the outer lumen 50b.

According to one preferred aspect of the invention, the most distal portion of the outer lumen 50b (above the tip) may not include holes, thereby forming a reservoir at the bottom of the outer lumen 50b; i.e., at the proximal end of the tip. The reservoir may then be filled a slow release anticoagulant agent which will slowly release an anticoagulant when blood is stationary in the outer lumen 50b (i.e., when hemodialysis is not being performed). The slow release of anticoagulant will prevent clots from forming and clogging the radial holes 60a, and could eliminate the need for a heparin flush procedure. The reservoir may take different forms as desired. For example, the reservoir may be a simple polymer matrix such as silicone rubber which is compounded with an anticoagulant and then cured. Alternatively, the matrix may take the form of a controlled release mechanism encapsulated in a semipermeable membrane.

According to another aspect of the invention, the inner lumen 50a and outer lumen 50b are sized so that the cross sectional flow area of the outer lumen 50b (i.e., the cross sectional area defined by the inner diameter of the outer lumen minus the cross sectional area defined by the outer diameter of the inner lumen) is larger than the cross sectional flow area of the inner lumen 50a (i.e., the cross sectional area defined by the inner diameter of the inner lumen). It has been found that with such an arrangement, a higher balanced blood flow rate is obtainable, as without such an arrangement, the surface areas presented by the outer surface of the inner lumen and the inner surface of the outer lumen, provide drag on the flow in the outer lumen and tend to cause a reduction in the flow through the outer lumen. While it is preferable to arrange the flow area in the outer lumen to be anywhere between ten and eighty percent greater than the flow area in the inner lumen, a more limited range of thirty to sixty percent shows better results. In fact, in the preferred embodiment, with typically catheter sizes, the flow area of the outer lumen is in a range of approximately forty to fifty percent larger than the flow area of the inner lumen. For example, in one of the presently preferred embodiments, the outer lumen has a diameter which is more than $\sqrt{2}$ times the diameter of the inner lumen. According to one example, the inner lumen 50a may be made of a polyurethane having a Shore 90A to 55D Durometer, and provided with an inner diameter of 0.080–0.085 inches and an outer diameter of 0.092 to 0.096 inches. The outer lumen 50b may be made of the same polyurethane material and provided with an inner diameter of 0.135 to 0.140 inches, and an outer diameter of 0.150 to 0.155 inches. With the provided diameters, when the inner lumen 50a is inserted in the outer lumen 50b, the outer lumen has a cross-sectional flow area which is approximately 40–50% larger than the cross-sectional flow area of the inner lumen. This additional flow area permits a flow rate of between 250 to 400 ml/min at 120 min Hg hydrostatic pressure, where lower flow rates would be obtained if the cross sectional flow areas of the inner lumen and outer lumen were to be the same.

Returning to FIGS. 2, 2a–2c, and 3, the proximal end of the preferred catheter 50 of the invention extends at least partially into an adapter 52 which sealingly divides the lumens into a non-concentric branched arrangement. In particular., the adapter 52 includes a channel 64 which has branches 64a, 64b, and 64c. According to one embodiment of the invention, branch 64c receives lumens 50a and 50b in their concentric arrangement, while branch 64a receives lumen 50a, and branch 64b receives lumen 50b. In this embodiment, the outer lumen 50b is provided with a hole 66 through which the inner lumen 50a passes as it enters branch 64b. The outer surface of inner lumen 50a is then sealingly fixed to the branch 64a so that fluid which might otherwise leak through the hole 66 may not flow up or down branch 64a. According to another embodiment, branch 64c receives lumens 50a and 50b in their concentric arrangement. However, outer lumen 50b branches (in a Y) so that channel branch 64b receives one branch of the outer lumen 50b only, while channel branch 64a receives the inner lumen 50a with the other branch of the outer lumen 50b therearound. With this arrangement, the outer diameter of inner lumen 50a is chosen to be substantially the same as the inner diameter of the branch of the outer lumen and the two are sealed together so that no fluid can flow therebetween. Regardless of the particular embodiment, it will be appreciated that the adapter receives the concentric lumens, and sealingly divides them out so that they assume a non-concentric branched arrangement.

Figure 3:
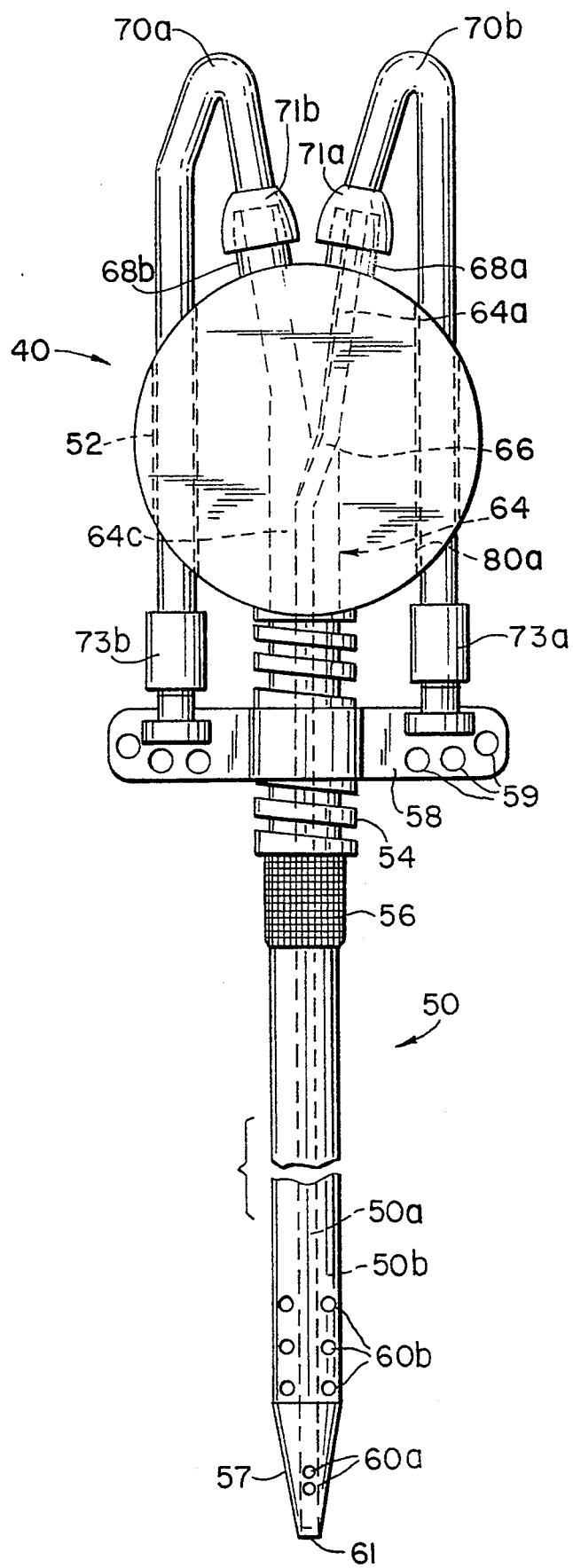
FIG. 3 is an enlarged schematic diagram of the hemodialysis catheter and catheter assembly of the invention in the usual closed position.

As shown in FIGS. 2 and 3, the lumens 50a and 50b preferably extend through the adapter 52 and terminate at nipples 68a, 68b which extend from the adapter. It will be appreciated, however, that while not preferred, it is possible to terminate the lumens inside the adapter channels, with the adapter channels serving to actually carry blood. The nipples 68a and 68b are provided as a convenient mating mechanism for flexible extenders 53a, 53b. The flexible extenders are preferably made from silicone rubber, although other soft resilient materials such as polyurethanes, polyolefins, and the like may be used. As indicated by FIGS. 2 and 3, the flexible extenders must be soft enough to kink or bend sufficiently so as to stem all fluid flow through the extender (as indicated at 70a, 70b of FIG. 3), while being resilient enough to resume a position which permits fluid flow therethrough (as seen in FIG. 2). The flexible extenders include first ends 71a, 71b which mate with nipples 68a, 68b, and second ends 73a, 73b which terminate in fluid connectors such as a male or female luer slip or luer lock 75a, 75b. In this manner, the catheter assembly 40 is easily coupled to other fluid flow lines (not shown) which are typically used in conjunction with hemodialysis machines.

Figure 2B:
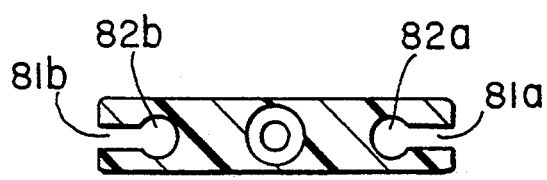
Figure 2C:
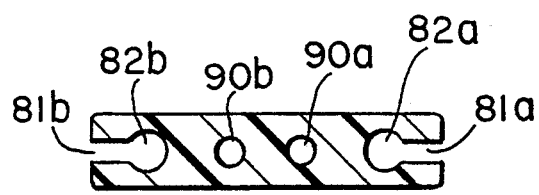

In order to hold the fluid connectors in a kinked position, the adapter 52 is preferably provided with grooves 80a, 80b. As shown in FIGS. 2b and 2c, grooves 80a, 80b have smaller diameter sections 81a, 81b through which the flexible extenders may be forced, and larger diameter sections 82a, 82b which hold the connectors without significantly squeezing them. If properly dimensioned, the flexible extenders will not slip through the grooves in the adapter and open the closed kinks because connectors 75a, 75b at the end of the extenders are of a larger diameter than the larger diameter sections 82a, 82b of the grooves and will act as a stop. It will be appreciated that adapter 52 is preferably formed as a flat disk of polished rigid plastic such as polycarbonate or polyurethane of Shore 55D to 75D Durometer with smooth outer surfaces. The arrangement is not unsightly, and because of its smooth surface is not uncomfortable for the patient.

Because the adapter 52 may be formed as a molding around the catheter 50, as aforementioned, the catheter 50 is preferably provided with a strain relief 54 which is adherently coupled to both the adapter 52 and the catheter 50. The .catheter is also preferably provided with a porous polyurethane mesh 56 along a portion of its outer surface which is intended to be in contact with the skin (fascia) of the patient. The polyurethane mesh is preferably spun according to the method disclosed in U.S. Pat. No. 4,475,972 to Wong, and is both biocompatible and substantially biostable so that the catheter may remain in the patient without disintegrating and without causing infection. In fact, the mesh 56 acts as a scaffold for tissue ingrowth, thereby eliminating the sinus tract which usually occurs when smooth tubes are placed percutaneously, and reducing risk of infection. The mesh 30 can contain or be impregnated with bactericides, antibiotics, and other drugs such as protamine and like, or sputter coated with a bactericidal agent such as silver, silver-nitrate, or cyclohexadine to further reduce risk of infection.

As also seen in FIGS. 2 and 3, the catheter 50 may be provided with a winged fixation device 58. While the winged fixation device 58 may not be necessary when the porous mesh 56 is provided, standard hemodialysis catheters are,provided with such devices. The winged fixation device 58 is provided with holes 59 for suturing as is known in the art.

There have been disclosed herein a hemodialysis catheter and catheter assembly. While particular embodiments of the invention have been described, it is not intended that the invention be limited exactly thereto, as it is intended that the invention be broad in scope as the art will allow. Thus, while particular materials were disclosed with reference to different aspects of the invention, it will be appreciated that other materials could be used; especially with reference to the adapter disk., Also, while particular geometries of the catheter and adapter disk were disclosed, it will be appreciated that other geometries could be utilized. For example, the inflow catheter could be provided with distal opening which extend through the flexible tip. Also, the adapter could be square, oblong, or otherwise shaped, and instead of having nipples, could be provided with male or female luer slips or locks or other mating mechanisms either external or internal the adapter. Therefore, it is apparent to those skilled in the art that additional changes and modifications may be made to the invention as described in the specification without departing from the spirit and scope of the invention.

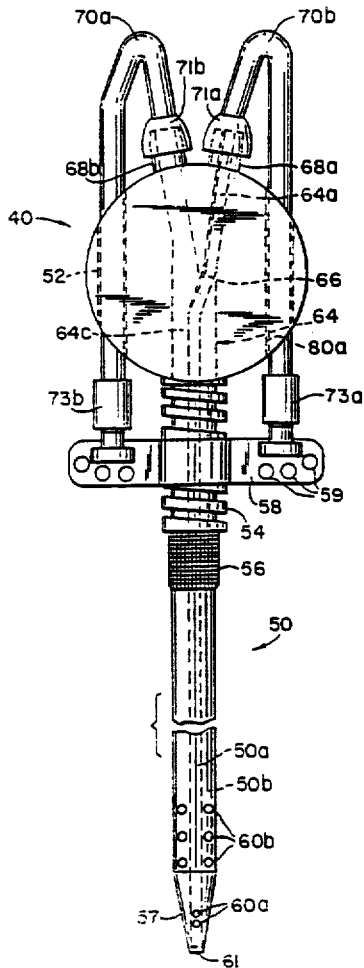

I claim:

1. A hemodialysis catheter, comprising:
   a) a first hollow lumen means of a first diameter and having proximal and distal ends, said first hollow lumen means defining a first flow path from said proximal end to said distal end, said first hollow lumen means for holding fluid flowing in a first direction and having at least one distal opening and a proximal opening;
   b) a second hollow lumen means of a second diameter smaller than said first diameter and extending within said first hollow lumen and through said distal end of said first hollow lumen means, and said second hollow lumen means extending outside said first flow path distal of said proximal end, said second hollow lumen means defining a second flow path with said first flow path and said second flow paths being separate from each other, said second hollow means for holding fluid flowing in a second direction opposite said first direction and having at least one distal opening and a proximal opening; and
   c) a porous polyurethane mesh located along a portion of an outer surface of said first hollow lumen means which is intended to be in contact with the skin of a patient.

2. A hemodialysis catheter according to claim 1, wherein:
   said first hollow lumen means is for holding fluid flowing from said distal end to said proximal end of said first hollow lumen means.

3. A hemodialysis catheter according to claim 2, wherein:
   said at least one distal opening in said first hollow lumen means comprises a plurality of circumferential distal openings.

4. A hemodialysis catheter according to claim 2, wherein:
   said at least one distal opening in said said second hollow lumen means comprises a plurality of circumferential distal openings and an axial distal opening.

5. A hemodialysis catheter according to claim 2, further comprising: c) a substantially solid atraumatic tapered tip portion, said tip portion adjacent and distal said distal end of said first hollow lumen means, and surrounding said distal end of said second hollow lumen means.

6. A hemodialysis catheter according to claim 5, wherein:
   said at least one distal opening in said first hollow lumen means comprises a plurality of circumferential distal openings.

7. A hemodialysis catheter according to claim 5, wherein:
   said at least one distal opening in said said second hollow lumen means comprises a plurality of circumferential distal openings and an axial distal opening, said tip portion having circumferential openings corresponding to and in fluid communication with said circumferential distal openings of said second hollow lumen means.

8. A hemodialysis catheter according to claim 7, wherein:
   said tip portion tapers as it extends distally from an outside diameter substantially the same as the outside diameter of said first hollow lumen means to the diameter of the outside of said second hollow lumen means.

9. A hemodialysis catheter according to claim 1, wherein:
   said mesh is sputter coated or impregnating with a bactericide.

10. A hemodialysis catheter according to claim 1, wherein:
    said first diameter is greater than $\sqrt{2}$ times said second diameter.

11. A hemodialysis catheter according to claim 10, wherein:
    a first fluid flow cross section through said first hollow lumen means is between thirty and fifty percent larger than a second fluid flow cross section through said second hollow lumen means.

12. A hemodialysis catheter according to claim 1, wherein:
    said first hollow lumen means has a cylindrical outer wall with a hole adjacent to its proximal end, and said second hollow lumen means extends through said hole.

13. A hemodialysis catheter according to claim 1, wherein:
    said distal end of said outer lumen constitutes a reservoir containing a slow release anticoagulant.

14. A hemodialysis catheter assembly comprising:
    a) a catheter having
       i) a first hollow lumen means of a first diameter and having proximal and distal ends, said first hollow lumen means defining a first flow path from said proximal end to said distal end, said first hollow lumen means for holding fluid flowing in a first direction and having at least one distal opening and a proximal opening and
       ii) a second hollow lumen means of a second diameter smaller than said first diameter and extending within said first hollow lumen and through said distal end of said first hollow lumen means, said second hollow lumen means defining a second flow path with said first flow path and said second flow paths being separate from each other, said second hollow means for holding fluid flowing in a second direction opposite said first direction and having at least one distal opening and a proximal opening; and
    b) adapter means comprising a substantially flat disk having a channel for receiving said first hollow lumen means with said second hollow lumen means therein, and for sealingly dividing said second hollow lumen means out from said first hollow lumen means such that said first and second hollow lumen means assume a branched relationship.

15. A hemodialysis catheter assembly according to claim 14, wherein:
    said channel has a first portion which receives said first hollow lumen means with said second hollow lumen means therein, a second portion which receives only said first hollow lumen means, and a third portion through which only said second hollow lumen means extends completely therethrough.

16. A hemodialysis catheter assembly according to claim 15, further comprising:
   c) first and second resilient flexible extenders, each extender having a proximal end coupled to proximal ends of respective of said first and second hollow lumen means, and each extender having a distal end having fluid coupling means for coupling to a hemodialysis means, wherein said extenders are sufficiently flexible such that in a first position they are doubled over and prevent fluid flow therethrough, and in a second position they permit fluid flow therethrough.

17. A hemodialysis catheter assembly according to claim 16, wherein:
   said adapter means has first and second grooves which receive and hold said first and second resilient flexible extenders in said first position.

18. A hemodialysis catheter assembly according to claim 16, wherein:
   said second hollow lumen means is substantially concentric with said first hollow lumen means along a portion thereof.

19. A hemodialysis catheter according to claim 14, wherein:
   said first direction is from said distal end to said proximal end of said first hollow lumen means.

20. A hemodialysis catheter according to claim 14, wherein:
   said at least one distal opening in said first hollow lumen means comprises a plurality of circumferential distal openings.

21. A hemodialysis catheter according to claim 14, wherein:
   said at least one distal opening in said said second hollow lumen means comprises a plurality of circumferential distal openings and an axial distal opening.

22. A hemodialysis catheter according to claim 14, further comprising:
   a porous polyurethane mesh located along a portion of an outer surface of said first hollow lumen means which is intended to be in contact with the skin of a patient.

23. A hemodialysis catheter according to claim 14, wherein:
   a first fluid flow cross section through said first hollow lumen means is between thirty and fifty percent larger than a second fluid flow cross section through said second hollow lumen means.

24. A hemodialysis catheter according to claim 14, wherein:
   said first hollow lumen means has a cylindrical outer wall with a hole adjacent to its proximal end, and said second hollow lumen means extends through said hole.

25. A hemodialysis catheter according to claim 14, wherein:
   said distal end of said outer lumen constitutes a reservoir containing a slow release anticoagulant.

26. A hemodialysis catheter assembly comprising:
   a) a catheter having
      i) a first hollow lumen means of a first diameter and having proximal and distal ends, said first hollow lumen means defining a first flow path from said proximal end to said distal end, said first hollow lumen means for holding fluid flowing in a first direction and having at least one distal opening and a proximal opening and
      ii) a second hollow lumen means of a second diameter smaller than said first diameter and extending within said first hollow lumen and through said distal end of said first hollow lumen means, said second hollow lumen means defining a second flow path with said first flow path and said second flow paths being separate from each other, said second hollow means for holding fluid flowing in a second direction opposite said first direction and having at least one distal opening and a proximal opening;
   b) adapter means having a channel for receiving said first hollow lumen means with said second hollow lumen means therein, and for sealingly dividing said second hollow lumen means out from said first hollow lumen means such that said first and second hollow lumen means assume a branched relationship; and
   c) a substantially solid atraumatic tapered tip portion, said tip portion adjacent and distal said distal end of said first hollow lumen means, and surrounding said distal end of said second hollow lumen means, wherein
      said at least one distal opening in said first hollow lumen means comprises a plurality of circumferential distal openings,
      said at least one distal opening in said said second hollow lumen means comprises a plurality of circumferential distal openings and an axial distal opening, said tip portion having circumferential openings corresponding to and in fluid communication with said circumferential distal openings of said second hollow lumen means, and
      said tip portion tapers as it extends distally from an outside diameter substantially the same as the outside diameter of said first hollow lumen means to the diameter of the outside of said second hollow lumen means.

27. A hemodialysis catheter assembly comprising:
   a) a catheter having
      i) a first hollow lumen means of a first diameter and having proximal and distal ends, said first hollow lumen means defining a first flow path from said proximal end to said distal end, said first hollow lumen means for holding fluid flowing in a first direction and having at least one distal opening and a proximal opening and
      ii) a second hollow lumen means of a second diameter smaller than said first diameter and extending within said first hollow lumen and through said distal end of said first hollow lumen means, said second hollow lumen means defining a second flow path with said first flow path and said second flow paths being separate from each other, said second hollow means for holding fluid flowing in a second direction opposite said first direction and having at least one distal opening and a proximal opening;
   b) adapter means having a channel for receiving said first hollow lumen means with said second hollow lumen means therein, and for sealingly dividing said second hollow lumen means out from said first hollow lumen means such that said first and second hollow lumen means assume a branched relationship; and c) first and second resilient flexible extenders, each extender having a proximal end coupled to proximal ends of respective of said first and second hollow lumen means, and each extender having a distal end having fluid coupling means for coupling to a hemodialysis means, wherein said extenders are sufficiently flexible such that in a first position they are doubled over and prevent fluid flow therethrough, and in a second position they permit fluid flow therethrough, wherein, said adapter means has first and second grooves which receive and hold said first and second resilient flexible extenders in said first position.

28. A hemodialysis catheter assembly according to claim 27, where in:
said channel has a first portion which receives said first hollow lumen means with said second hollow lumen means therein, a second portion which receives only said first hollow lumen means, and a third portion through which only said second hollow lumen means extends completely therethrough.

29. A hemodialysis catheter assembly according to claim 27, wherein:
said adapter means comprises a substantially flat plastic disk.

30. A hemodialysis catheter according to claim 27, further comprising:
d) a substantially solid atraumatic tapered tip portion, said tip portion adjacent and distal said distal end of said first hollow lumen means, and surrounding said distal end of said second hollow lumen means.

31. A hemodialysis catheter according to claim 30, wherein:
said at least one distal opening in said first hollow lumen means comprises a plurality of circumferential distal openings, and
said at least one distal opening in said said second hollow lumen means comprises a plurality of circumferential distal openings and an axial distal opening, said tip portion having circumferential openings corresponding to and in fluid communication with said circumferential distal openings of said second hollow lumen means.

32. A hemodialysis catheter according to claim 30, further comprising:
e) a porous polyurethane mesh located along a portion of an outer surface of said first hollow lumen means which is intended to be in contact with the skin of a patient.

33. A hemodialysis catheter according to claim 27, wherein:
a first fluid flow cross section through said first hollow lumen means is between thirty and fifty percent larger than a second fluid flow cross section through said second hollow lumen means.

34. A hemodialysis catheter, comprising:
a) a first hollow lumen means having proximal and distal ends, said first hollow lumen means defining a first flow path from said proximal end to said distal end, said first hollow lumen means for holding fluid flowing in a first direction and having at least one distal opening and a proximal opening;
b) a second hollow lumen means having proximal and distal ends, said second hollow lumen means defining a second flow path with said first flow path and said second flow paths being separate from each other, said second hollow means for holding fluid flowing in a second direction opposite said first direction and having at least one distal opening and a proximal opening; and
c) a porous polyurethane mesh located along a portion of an outer surface of said first hollow lumen means which is intended to be in contact with the skin of a patient.

35. A hemodialysis catheter assembly comprising:
a) a catheter having
i) a first hollow lumen means having proximal and distal ends, said first hollow lumen means defining a first flow path from said proximal end to said distal end, said first hollow lumen means for holding fluid flowing in a first direction and having at least one distal opening and a proximal opening and
ii) a second hollow lumen means having proximal and distal ends, said second hollow lumen means defining a second flow path with said first flow path and said second flow paths being separate from each other, said second hollow means for holding fluid flowing in a second direction opposite said first direction and having at least one distal opening and a proximal opening; and
b) adapter means for receiving said first and second hollow lumen means therein, and for sealingly dividing said first and second hollow lumen means such that said first and second hollow lumen means assume a branched relationship, said adapter means comprising a substantially flat plastic disk.

36. A hemodialysis catheter assembly comprising:
a) a catheter having
i) a first hollow lumen means having proximal and distal ends, said first hollow lumen means defining a first flow path from said proximal end to said distal end, said first hollow lumen means for holding fluid flowing in a first direction and having at least one distal opening and a proximal opening and
ii) a second hollow lumen means having proximal and distal ends, said second hollow lumen means defining a second flow path with said first flow path and said second flow paths being separate from each other, said second hollow means for holding fluid flowing in a second direction opposite said first direction and having at least one distal opening and a proximal opening; and
b) adapter means for receiving said first and second hollow lumen means therein, and for sealingly dividing said first and second hollow lumen means such that said first and second hollow lumen means assume a branched relationship; and
c) first and second resilient flexible extenders, each extender having a proximal end coupled to proximal ends of respective of said first and second hollow lumen means, and each extender having a distal end having fluid coupling means for coupling to a hemodialysis means, wherein said extenders are sufficiently flexible such that in a first position they are doubled over and prevent fluid flow therethrough, and in a second position they permit fluid flow therethrough, wherein
said adapter means has first and second grooves which receive and hold said first and second resilient flexible extenders in said first position.

37. A hemodialysis catheter assembly comprising:
a) a catheter having i) a first hollow lumen means having proximal and distal ends, said first hollow lumen means defining a first flow path from said proximal end to said distal end, said first hollow lumen means for holding fluid flowing in a first direction and having at least one distal opening and a proximal opening and ii) a second hollow lumen means having proximal and distal ends, said second hollow lumen means defining a second flow path with said first flow path and said second flow paths being separate from each other, said second hollow means for holding fluid flowing in a second direction opposite said first direction and having at least one distal opening and a proximal opening; and b) adapter means for receiving said first and second hollow lumen means therein, and for sealingly dividing said first and second hollow lumen means such that said first and second hollow lumen means assume a branched relationship; and c) a substantially solid atraumatic tapered tip portion, said tip portion adjacent and distal said distal end of said first hollow lumen means, and surrounding said distal end of said second hollow lumen means, wherein said at least one distal opening in said first hollow lumen means comprises a plurality of circumferential distal openings, said at least one distal opening in said said second hollow lumen means comprises a plurality of circumferential distal openings and an axial distal opening, said tip portion having circumferential openings corresponding to and in fluid communication with said circumferential distal openings of said second hollow lumen means, and said tip portion tapers as it extends distally from an outside diameter substantially the same as the outside diameter of said first hollow lumen means to the diameter of the outside of said second hollow lumen means.

* * * * *

UNITED STATES PATENT AND TRADEMARK OFFICE
CERTIFICATE OF CORRECTION

PATENT NO : 5,360,397

DATED : November 1, 1994

INVENTOR(S) : Leonard Pinchuk

It is certified that error appears in the above-identified patent and that said Letters Patent is hereby corrected as shown below:

The title page showing the illustrative figure should be deleted to be replaced with the attached title page.

Signed and Sealed this

Twenty-first Day of February, 1995

Attest:

BRUCE LEHMAN

Attesting Officer

Commissioner of Patents and Trademarks

United States Patent [19]

Pinchuk

[11] Patent Number: 5,360,397
[45] Date of Patent: Nov. 1, 1994

[54] HEMODIAYLSIS CATHETER AND CATHETER ASSEMBLY
[75] Inventor: Leonard Pinchuk, Miami, Fla.
[73] Assignee: Corvita Corporation, Miami, Fla.
[21] Appl. No.: 87,173
[22] Filed: Jul. 2, 1993
[51] Int. Cl.⁵ .............................................. A61M 1/00
[52] U.S. Cl. ................................. 604/27; 604/43; 604/266
[58] Field of Search ............... 604/27, 43, 174, 180, 604/266, 280, 284

[56] References Cited
U.S. PATENT DOCUMENTS

| | | | |
|---|---|---|---|
| 3,929,126 | 12/1975 | Corsqut | 604/43 |
| 4,134,402 | 1/1979 | Mahurkar | 128/214 R |
| 4,323,071 | 4/1982 | Simpson et al. | 128/343 |
| 4,583,968 | 4/1986 | Mahurkar | 604/43 |
| 4,692,141 | 9/1987 | Mahurkar | 604/43 |
| 4,871,357 | 10/1989 | Hsu et al. | 604/266 |
| 4,895,561 | 1/1990 | Kar | 604/43 |
| 4,935,006 | 6/1990 | Hasson | 604/43 |
| 5,188,593 | 2/1993 | Martin | 604/43 |

Primary Examiner—Jerome L. Kruter
Attorney, Agent, or Firm—David P. Gordon

[57] ABSTRACT

A hemodialysis catheter having a concentric outer lumen for inflow and a concentric inner lumen for outflow is disclosed. The hemodialysis catheter is used in conjunction with an adapter and with flexible extenders as a catheter assembly. The adapter has channels into which the concentric lumens extend and sealingly divides the lumens into a non-concentric branched arrangement. The flexible extenders couple to the branched lumens or to the adapter and may be doubled over and fastened in grooves in the adapter to stop fluid flow through the catheter. The flexible extenders preferably terminate in coupling mechanisms such as luer slips or luer locks. The catheter is provided with a soft atraumatic tip which has radial holes and a distal hole coupled to the inner lumen of the catheter. The outer lumen which terminates proximally of the tip also has radial holes. The catheter is preferably provided with a porous biocompatible and biostable polyurethane mesh along a portion of its outer surface which is intended to be in contact with the skin of the patient. The mesh may be sputter coated or impregnated with a bactericide.

37 Claims, 4 Drawing Sheets